(12) United States Patent
Fujimura et al.

(10) Patent No.: US 7,932,398 B2
(45) Date of Patent: Apr. 26, 2011

(54) SUBSTITUTED PHENYLETHYNYLGOLD-NITROGEN-CONTAINING HETEROCYCLIC CARBENE COMPLEX

(75) Inventors: Osamu Fujimura, Ichihara (JP); Kenji Fukunaga, Ichihara (JP); Takashi Honma, Ichihara (JP); Toshikazu Machida, Ichihara (JP)

(73) Assignee: Ube Industries, Ltd., Ube-Shi (JP)

( * ) Notice: Subject to any disclaimer, the term of this patent is extended or adjusted under 35 U.S.C. 154(b) by 78 days.

(21) Appl. No.: 12/302,499

(22) PCT Filed: May 25, 2007

(86) PCT No.: PCT/JP2007/060675
§ 371 (c)(1),
(2), (4) Date: Nov. 25, 2008

(87) PCT Pub. No.: WO2007/139001
PCT Pub. Date: Dec. 6, 2007

(65) Prior Publication Data
US 2009/0234130 A1      Sep. 17, 2009

(30) Foreign Application Priority Data
May 25, 2006   (JP) ................. 2006-145091

(51) Int. Cl.
*C07F 1/12*            (2006.01)
(52) U.S. Cl. ........................................ 548/103
(58) Field of Classification Search .............. 548/103
See application file for complete search history.

(56) References Cited

FOREIGN PATENT DOCUMENTS

| JP | 3-227954 A | 10/1991 |
|---|---|---|
| WO | WO-98/27064 A1 | 6/1998 |
| WO | WO-2006/080515 A1 | 8/2006 |

OTHER PUBLICATIONS

Wang, Harrison M. J. et al., Organometallics, 1999, 18 (7), pp. 1216-1223.
Singh, Sanjay et al., European Journal of Inorganic Chemistry, 2005, (15), pp. 3057-3062.
Cross, Ronald J. et al., J. Chem. Soc. Dalton Trans. 1986, pp. 411-414.
Jikken Kagaku Koza, 4th ed., Maruzen, vol. 18, 1991, pp. 455-457.
Arduengo, Anthony J. et al., J. Am. Chem. Soc. 1992, 114, pp. 5530-5534.
Havens, Stephen J. et al., J. Org. Chem. 1985, 50, pp. 1763-1765.
Jikken Kagaku Koza, 4th ed., Maruzen, vol. 22, 1991, pp. 43-54.
Jikken Kagaku Koza, 4th ed., Maruzen, vol. 22, 1991, pp. 138-151.

*Primary Examiner* — Kamal A Saeed
*Assistant Examiner* — Kristin Bianchi
(74) *Attorney, Agent, or Firm* — Birch, Stewart, Kolasch & Birch, LLP

(57) ABSTRACT

The present invention is directed to a substituted phenylethynylgold-nitrogen-containing heterocyclic carbene complex represented by the formula (1) or (2):

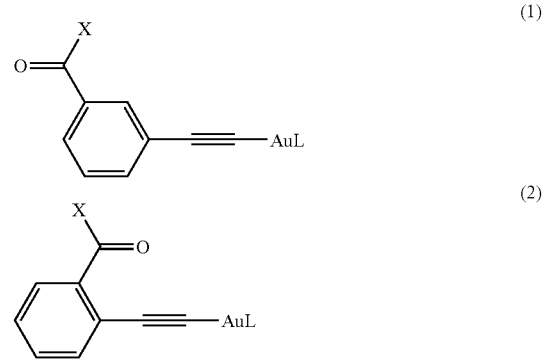

wherein L represents a nitrogen-containing heterocyclic carbene ligand, and X represents an alkyl group, a cycloalkyl group, an aryl group, an aralkyl group, a heterocyclic group, an alkoxy group, an aryloxy group, an alkylmercapto group, an arylmercapto group or a substituted amino group; and one or a plural number of hydrogen atoms on the carbon atom(s) of X are independently optionally replaced by a halogen atom, an alkyl group, a cycloalkyl group, an alkenyl group, an aryl group, an aralkyl group, an alkoxy group, an aryloxy group, an alkylmercapto group, an arylmercapto group or a substituted amino group.

10 Claims, No Drawings

SUBSTITUTED PHENYLETHYNYLGOLD-NITROGEN-CONTAINING HETEROCYCLIC CARBENE COMPLEX

FIELD OF THE INVENTION

The present invention relates to a substituted phenylethynylgold-nitrogen-containing heterocyclic carbene complex advantageously used as, e.g., a luminescent material for electroluminescent device (organic electro-luminescent device).

BACKGROUND ART

An organic electroluminescent device has recently attracted attention as a display device for high-performance flat color display. With respect to the luminescent material, a fluorescent material utilizing luminescence from the excitation singlet state of an emitting molecule is mainly used, and, for further improving the emission efficiency, the development of a phosphorescent material utilizing luminescence from the excitation triplet state is being vigorously made. However, the substituted ethynylgold-nitrogen-containing heterocyclic carbene complex of the present invention has not been known.

DISCLOSURE OF THE INVENTION

Problems to be Solved by the Invention

Accordingly, a task of the present invention is to provide a nonionic compound, advantageously used as, e.g., a luminescent material for organic luminescent device, having luminescence in a blue wavelength range of 460 nm or less essential to realize a full-color display and having a high melting point of 200° C. or more such that the material can endure Joulean heat generated in the application of a voltage.

Means to Solve the Problems

The above task of the present invention is achieved by a substituted phenylethynylgold-nitrogen-containing heterocyclic carbene complex represented by the following general formula (1) or (2):

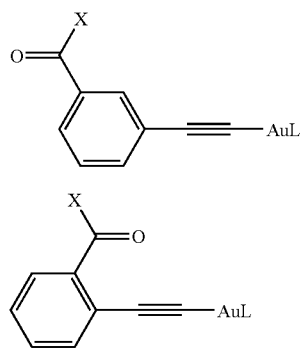

wherein L represents a nitrogen-containing heterocyclic carbene ligand and X represents an alkyl group, a cycloalkyl group, an aryl group, an aralkyl group, a heterocyclic group, an alkoxy group, an aryloxy group, an alkylmercapto group, an arylmercapto group or a substituted amino group; and one or a plural number of hydrogen atoms on the carbon atom(s) of X are independently optionally replaced by a halogen atom, an alkyl group, a cycloalkyl group, an alkenyl group, an aryl group, an aralkyl group, an alkoxy group, an aryloxy group, an alkylmercapto group, an arylmercapto group or a substituted amino group.

Effect of the Invention

According to the present invention, there can be provided a substituted phenylethynylgold-nitrogen-containing heterocyclic carbene complex advantageously used as, e.g., a luminescent material for organic electroluminescent device.

BEST MODE FOR CARRYING OUT THE INVENTION

The substituted phenylethynylgold-nitrogen-containing heterocyclic carbene complex of the present invention is represented by the general formula (1) or (2) above. In the general formula (1) or (2), L represents a nitrogen-containing heterocyclic carbene ligand. X represents an alkyl group, a cycloalkyl group, an aryl group, an aralkyl group, a heterocyclic group, an alkoxy group, an aryloxy group, an alkylmercapto group, an arylmercapto group or a substituted amino group.

With respect to the alkyl group, preferred is an alkyl group having 1 to 10 carbon atoms and examples include a methyl group, an ethyl group, a propyl group, a butyl group, a pentyl group, a hexyl group, a heptyl group, an octyl group, a nonyl group and a decyl group, Especially preferred is an alkyl group having 1 to 6 carbon atoms. These substituents include their isomers.

With respect to the cycloalkyl group, preferred is a cycloalkyl group having 3 to 12 carbon atoms and examples include a cyclopropyl group, a cyclobutyl group, a cyclopentyl group, a cyclohexyl group, a cycloheptyl group, a cyclooctyl group, a cyclononyl group, a cyclodecyl group, a cycloundecyl group and a cyclododecyl group.

With respect to the aryl group, preferred is an aryl group having 6 to 18 carbon atoms and examples include a phenyl group, a tolyl group, a xylyl group, a biphenyl group, an indenyl group, a naphthyl group, a dimethylnaphthyl group, an anthryl group, a phenanthryl group, a fluorenyl group, a pyrenyl group, a chrysenyl group and a naphthacenyl group. Especially preferred is an aryl group having 6 to 14 carbon atoms. These substituents include their isomers.

With respect to the aralkyl group, preferred is an aralkyl group having 7 to 20 carbon atoms and examples include a benzyl group, a phenethyl group, a naphthylmethyl group, an indenylmethyl group and a biphenylmethyl group.

With respect to the heterocyclic group, preferred is a saturated or unsaturated cyclic group containing at least one heteroatom selected from N, O and S and being comprised of a 3- to 10-membered ring and examples include a pyrrolyl group, a furyl group, a thienyl group, an indolyl group, a benzofuranyl group, a benzothiophenyl group, a pyridyl group, a pyrazinyl group, a pyrimidinyl group, a pyridazinyl group, a quinolyl group, an isoquinolyl group, a quinazolinyl group and a quinoxalinyl group.

With respect to the alkoxy group, preferred is an alkoxy group having 1 to 10 carbon atoms and examples include a methoxy group, an ethoxy group, a propoxy group, a butoxy group, a pentanoxy group, a hexanoxy group, a heptanoxy group, an octanoxy group, a nonanoxy group and a decanoxy group. Especially preferred is an alkoxy group having 1 to 6 carbon atoms. These substituents include their isomers.

With respect to the aryloxy group, preferred is an aryloxy group having 6 to 14 carbon atoms and examples include a phenoxy group, a tolyloxy group, a xylyloxy group and a naphthoxy group. These substituents include their isomers.

With respect to the alkylmercapto group, preferred is an alkylmercapto group having 1 to 6 carbon atoms and examples include a methylmercapto group, an ethylmercapto group, a propylmercapto group, a butylmercapto group, a pentylmercapto group and a hexylmercapto group. These substituents include their isomers.

With respect to the arylmercapto group, preferred is an arylmercapto group having 6 to 14 carbon atoms and examples include a phenylmercapto group, a tolylmercapto group, a xylylmercapto group and a naphthylmercapto group. These substituents include their isomers.

With respect to the substituted amino group, preferred is an amino group substituted with one group or two groups selected from an alkyl group having 1 to 6 carbon atoms, an aryl group having 6 to 14 carbon atoms and an aralkyl group having 7 to 20 carbon atoms. Particularly, examples include alkylamino groups having 1 to 6 carbon atoms such as a methylamino group, an ethylamino group, a propylamino group and a butylamino group, dialkylamino groups substituted with the same or different two alkyl groups each having 1 to 6 carbon atoms such as a dimethylamino group, a methylethylamino group, a diethylamino group and a dipropylamino group, arylamino groups having 6 to 14 carbon atoms such as a phenylamino group, a tolylamino group, a xylylamino group and a naphthylamino group, diarylamino groups substituted with the same or different two aryl groups each having 6 to 14 carbon atoms such as a diphenylamino group, a ditolylamino group and a dixylylamino group, aralkylamino groups having 7 to 20 carbon atoms such as a benzylamino group and a phenethylamino group, and diaralkylamino groups substituted with the same or different two aralkyl groups each having 7 to 20 carbon atoms such as a dibenzylamino group. These substituents include their isomers.

One or a plural number of hydrogen atoms on the carbon atom(s) of X are independently optionally replaced by a halogen atom, an alkyl group, a cycloalkyl group, an alkenyl group, an aryl group, an aralkyl group, an alkoxy group, an aryloxy group, an alkylmercapto group, an arylmercapto group or a substituted amino group.

Examples of the halogen atoms include a fluorine atom, a chlorine atom, a bromine atom and an iodine atom.

With respect to the alkyl group, preferred is an alkyl group having 1 to 20 carbon atoms, especially 1 to 12 carbon atoms and examples include a methyl group, an ethyl group, a propyl group, a butyl group, a pentyl group, a hexyl group, a heptyl group, an octyl group, a nonyl group, a decyl group, an undecyl group and a dodecyl group. Especially preferred is an alkyl group having 1 to 6 carbon atoms. These substituents include their isomers.

With respect to the cycloalkyl group, especially preferred is a cycloalkyl group having 3 to 7 carbon atoms and examples include a cyclopropyl group, a cyclobutyl group, a cyclopentyl group, a cyclohexyl group, a cyclopentyl group, a cyclohexyl group and a cycloheptyl group.

With respect to the alkenyl group, preferred is an alkenyl group having 2 to 20 carbon atoms, especially 2 to 12 carbon atoms and examples include a vinyl group, a propenyl group, a butenyl group, a pentenyl group, a hexenyl group, a heptenyl group, an octenyl group, a nonenyl group, a decenyl group, an undecenyl group and a dodecenyl group. These substituents include their isomers.

With respect to the aryl group, preferred is an aryl group having 6 to 20 carbon atoms, especially 6 to 16 carbon atoms and examples include a phenyl group, a tolyl group, a xylyl group, a naphthyl group, a dimethylnaphthyl group, an anthryl group, a phenanthryl group, a fluorenyl group and a pyrenyl group. These substituents include their isomers.

With respect to the aralkyl group, preferred is an aralkyl group having 7 to 20 carbon atoms and examples include a benzyl group, a phenethyl group, a naphthylmethyl group, an indenylmethyl group and a biphenylmethyl group.

With respect to the alkoxy group, especially preferred is an alkoxy group having 1 to 10 carbon atoms and examples include a methoxy group, an ethoxy group, a propoxy group, a butoxy group, a pentanoxy group, a hexanoxy group, a heptanoxy group, an octanoxy group, a nonanoxy group and a decanoxy group. These substituents include their isomers.

With respect to the aryloxy group, especially preferred is an aryloxy group having 6 to 14 carbon atoms and examples include a phenoxy group, a tolyloxy group, a xylyloxy group and a naphthoxy group. These substituents include their isomers.

With respect to the alkylmercapto group, preferred is an alkylmercapto group having 1 to 6 carbon atoms and examples include a methylmercapto group, an ethylmercapto group, a propylmercapto group, a butylmercapto group, a pentylmercapto group and a hexylmercapto group. These substituents include their isomers.

With respect to the arylmercapto group, preferred is an arylmercapto group having 6 to 14 carbon atoms and examples include a phenylmercapto group, a tolylmercapto group, a xylylmercapto group and a naphthylmercapto group. These substituents include their isomers.

With respect to the substituted amino group, preferred is an amino group substituted with one group or two groups selected from an alkyl group having 1 to 6 carbon atoms, an aryl group having 6 to 14 carbon atoms and an aralkyl group having 7 to 20 carbon atoms. Particularly, examples include alkylamino groups having 1 to 6 carbon atoms such as a methylamino group, an ethylamino group, a propylamino group and a butylamino group, dialkylamino groups substituted with the same or different two alkyl groups each having 1 to 6 carbon atoms such as a dimethylamino group, a methylethylamino group, a diethylamino group and a dipropylamino group, arylamino groups having 6 to 14 carbon atoms such as a phenylamino group, a tolylamino group, a xylylamino group and a naphthylamino group, diarylamino groups substituted with the same or different two aryl groups each having 6 to 14 carbon atoms such as a diphenylamino group, a ditolylamino group and a dixylylamino group, aralkylamino groups having 7 to 20 carbon atoms such as a benzylamino group and a phenethylamino group, and diaralkylamino groups substituted with the same or different two aralkyl groups each having 7 to 20 carbon atoms such as a dibenzylamino group. These substituents include their isomers.

When a plurality of hydrogen atoms on the carbon atom(s) of X are replaced by an alkyl group, an alkenyl group, an aryl group, an aralkyl group, an alkoxy group, an aryloxy group or a substituted amino group, the adjacent groups are optionally bonded together to form a ring.

When the adjacent groups are bonded together to form a ring, examples of the rings formed include a cyclopentene ring, a cyclohexene ring, a cycloheptene ring, a benzene ring, a naphthalene ring, a tetrahydrofuran ring, a benzopyran ring, an N-methylpyrrolidine ring and an N-methylpiperidine ring.

It is preferred that X is selected from an alkyl group having 1 to 6 carbon atoms, an aryl group having 6 to 14 carbon atoms, an alkoxy group having 1 to 6 carbon atoms, an aryloxy group having 6 to 14 carbon atoms, an alkylmercapto group having 1 to 6 carbon atoms, an arylmercapto group having 6 to 14 carbon atoms, a dialkylamino group substituted with the same or different two alkyl groups each having 1 to 6 carbon atoms and a diarylamino group substituted with the same or different two aryl groups each having 6 to 14 carbon atoms and one or a plural number of hydrogen atoms on the carbon atom(s) of X are independently optionally replaced by a fluorine atom, a chlorine atom, a bromine atom or an iodine atom. With respect to X, especially preferred is a methyl group, a phenyl group, a fluorophenyl group, a methoxy group, a phenoxy group, a methylmercapto group, a phenylmercapto group, a diethylamino group or a diphenylamino group.

The nitrogen-containing heterocyclic carbene ligand is represented by the following general formula (3) or (4):

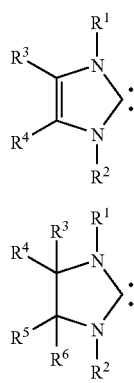

(3)

(4)

wherein each of $R^1$ and $R^2$ independently represents an alkyl group, a cycloalkyl group, a polycycloalkyl group or an aryl group, and each of $R^3$, $R^4$, $R^5$ and $R^6$ independently represents a hydrogen atom, a halogen atom, an alkyl group, an alkenyl group, an aryl group, an aralkyl group, an alkoxy group, an aryloxy group, a nitro group, a cyano group or a dialkylamino group, the adjacent groups in $R^3$, $R^1$, $R^5$ and $R^6$ are optionally bonded together, so that the adjacent groups and the carbon atom(s) to which the groups are bonded together form a ring; and, when $R^1$ to $R^6$ represent a group containing a carbon atom(s), one or a plural number of hydrogen atoms on the carbon atom(s) of the group are optionally replaced by a halogen atom, an alkyl group, a cycloalkyl group, an alkenyl group, an aryl group, an aralkyl group, an alkoxy group or an aryloxy group.

In the general formula (3) or (4), each of $R^1$ and $R^2$ represents an alkyl group, a cycloalkyl group, a polycycloalkyl group or an aryl group and the alkyl group, cycloalkyl group and aryl group are as defined above for those by which the hydrogen atom(s) on the carbon atom(s) of X is(are) optionally replaced.

With respect to the polycycloalkyl group, preferred is a polycycloalkyl group having 6 to 10 carbon atoms and examples include a bicyclo-[2.1.1]-hexyl group, a bicyclo-[2.2.1]-heptyl group, a bicyclo-[2.2.2]-octyl group, a bicyclo-[3.3.0]-octyl group, a bicyclo-[4.3.0]-nonyl group, a bicyclo-[4.4.0]-octyl group and an adamantyl group.

Each of $R^3$, $R^4$, $R^5$ and $R^6$ represents a hydrogen atom, a halogen atom, an alkyl group, an alkenyl group, an aryl group, an aralkyl group, an alkoxy group, an aryloxy group, a nitro group, a cyano group or a dialkylamino group and the alkyl group, alkenyl group, aryl group, aralkyl group, alkoxy group, aryloxy group and dialkylamino group are as defined above for those by which the hydrogen atom(s) on the carbon atom(s) of X is(are) optionally replaced.

The adjacent groups in $R^3$, $R^4$, $R^5$ and $R^6$ are optionally bonded together, so that the adjacent groups and the carbon atom(s) to which the groups are bonded together form a ring. In the general formula (3), when $R^3$ and $R^4$ and the carbon atoms to which they are bonded together form a ring, examples of the rings formed include carbon rings having 5 to 10 carbon atoms such as a cyclopentene ring, a cyclohexene ring, a cycloheptene ring, a benzene ring and a naphthalene ring. In the general formula (4), when $R^3$ (or $R^4$) and $R^5$ (or $R^6$) and the carbon atoms to which they are bonded together form a ring, examples of the rings formed include carbon rings having 5 to 10 carbon atoms such as a cyclopentane ring, a cyclohexane ring, a cycloheptane ring, a benzene ring and a naphthalene ring.

When $R^1$ to $R^6$ represent a group containing a carbon atom(s), one or a plural number of hydrogen atoms on the carbon atom(s) of the group are optionally replaced by a halogen atom, an alkyl group, a cycloalkyl group, an alkenyl group, an aryl group, an aralkyl group, an alkoxy group or an aryloxy group and these groups are as defined above for those by which the hydrogen atom(s) on the carbon atom(s) of X is(are) optionally replaced. Of these, it is preferred that each of $R^1$ and $R^2$ is selected from an alkyl group having 1 to 6 carbon atoms, an aryl group having 6 to 14 carbon atoms and a polycycloalkyl group having 6 to 10 carbon atoms and one or a plural number of hydrogen atoms on the carbon atom(s) of the aryl group are independently optionally replaced by an alkyl group having 1 to 6 carbon atoms. Each of $R^1$ and $R^2$ is especially preferably a tert-butyl group, a 2,6-diisopropylphenyl group, a 2,4,6-trimethylphenyl group or an adamantyl group. Each of $R^3$, $R^4$, $R^5$ and $R^6$ is preferably a hydrogen atom or a halogen atom, especially preferably a hydrogen atom or a chlorine atom.

In the present invention, specific examples of the nitrogen-containing heterocyclic carbene ligands (L) include compounds represented by the following formulae (5) to (14).

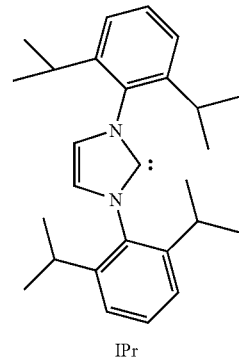

(5)

IPr

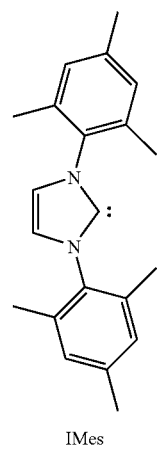

(6)

IMes

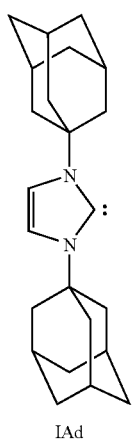
IAd
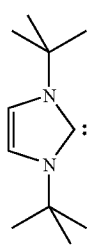
ItBu
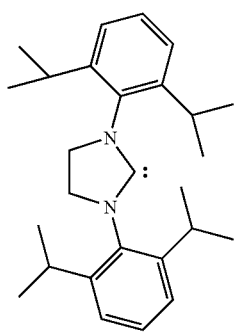
H₂—IPr
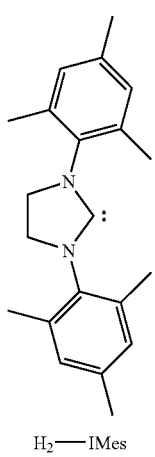
H₂—IMes
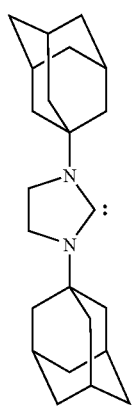
H₂—IAd
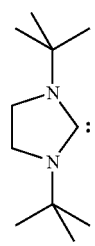
H₂—ItBu
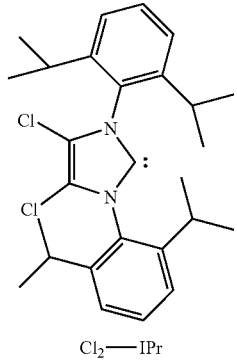
Cl₂—IPr
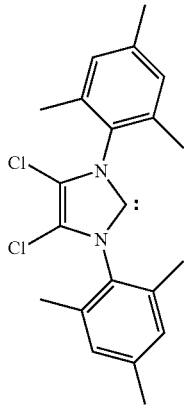
Cl₂—IMes
The substituted phenylethynylgold-nitrogen-containing heterocyclic carbene complex represented by the general formula (1) or (2) of the present invention is obtained as shown in, for example, the following reaction scheme (1):

[Reaction scheme (1)]

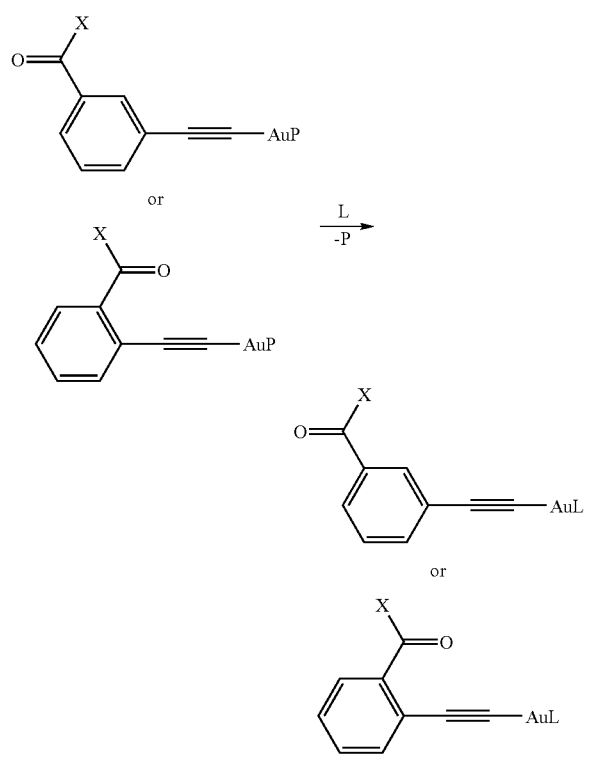

wherein X and L are as defined above and P represents a monodentate phosphine ligand, by reacting a substituted phenylethynylgold-phosphine complex represented by the general formula (Ia) or (Ib) with a nitrogen-containing heterocyclic carbene ligand (L).

Examples of the monodentate phosphine ligands (P) include bis(pentafluorophenyl)phenylphosphine, (4-bromophenyl)diphenylphosphine, diallylphenylphosphine, dicyclohexylphenylphosphine, diethylphenylphosphine, 4-(dimethylamino)phenyldiphenylphosphine, dimethylphenylphosphine, diphenyl(2-methoxyphenyl)phosphine, diphenyl(pentafluorophenyl)phosphine, diphenylpropylphosphine, diphenyl-2-pyridylphosphine, diphenyl(p-tolyl)phosphine, diphenylvinylphosphine, ethyldiphenylphosphine, isopropyldiphenylphosphine, methyldiphenylphosphine, tribenzylphosphinet tributylphosphine, tri-t-butylphosphine, tricyclohexylphosphine, tricyclopentylphosphine, triethylphosphine, tri-2-furylphosphine, triisobutylphosphine, triisopropylphosphine, tripropylphosphine, trimethylphosphine, trioctylphosphine, triphenylphosphine, tris(4-chlorophenyl)phosphine, tris(3-chlorophenyl)phosphine, tris(2,6-dimethoxyphenyl)phosphine, tris(4-fluorophenyl)phosphine, tris(3-fluorophenyl)phosphine, tris(4-methoxyphenyl)phosphine, tris(3-methoxyphenyl)phosphine, tris(2-methoxyphenyl)phosphine, tris(4-trifluoromethylphenyl)phosphine, tris(pentafluorophenyl)phosphine, tris(2,4,6-trimethoxyphenyl)phosphine, tris(2,4,6-trimethylphenyl)phosphine, tri-m-tolylphosphine, tri-o-tolylphosphine, tri-p-tolylphosphine, benzyldiphenylphosphine, bis(2-methoxyphenyl)phenylphosphine, diphenylcyclohexylphosphine, 2-(di-t-butylphosphino)biphenyl, 2-(dicyclohexylphosphino)biphenyl, neomenthyldiphenylphosphine, p-tolyldiphenylphosphine, triallylphosphine, tris(2,4,4-trimethylpentyl)phosphine, tri(1-naphthyl)phosphine, tris(hydroxymethyl)phosphine and tris(hydroxypropyl)phosphine. With respect to the monodentate phosphine ligand, a product commercially available can be directly used.

The substituted phenylethynylgold-phosphine complex is obtained as shown in, for example, the following reaction scheme (2):

[Reaction scheme (2)]

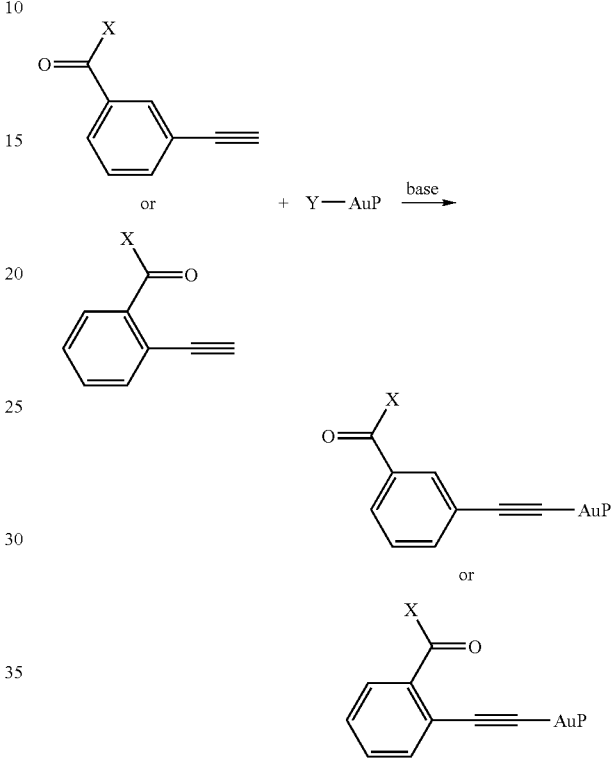

wherein X and P are as defined above and Y represents a halogen atom, by reacting a gold-halogenophosphine complex with a substituted phenylethyn (see, for example, Journal of Chemical Society, Dalton Trans., 1986, 411).

The gold-halogenophosphine complex can be synthesized by a known method (see, for example, Lecture on Experimental Chemistry, Fourth edition, published by Maruzen Co., Ltd., page 455, vol. 18 (1991)).

With respect to the nitrogen-containing heterocyclic carbene ligand, a product commercially available may be directly used or, for example, a product synthesized by a known method may be used (see, for example, J. Am. Chem. Soc., 114, 5530 (1992) and WO 98/27064).

The substituted phenylethyn compound represented by the general formula (15) or (16):

(15)

-continued

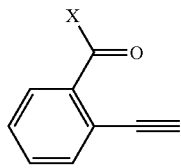
(16)

wherein X is as defined above,
can be synthesized as shown in, for example, the following reaction scheme (3):

[Reaction scheme (3)]

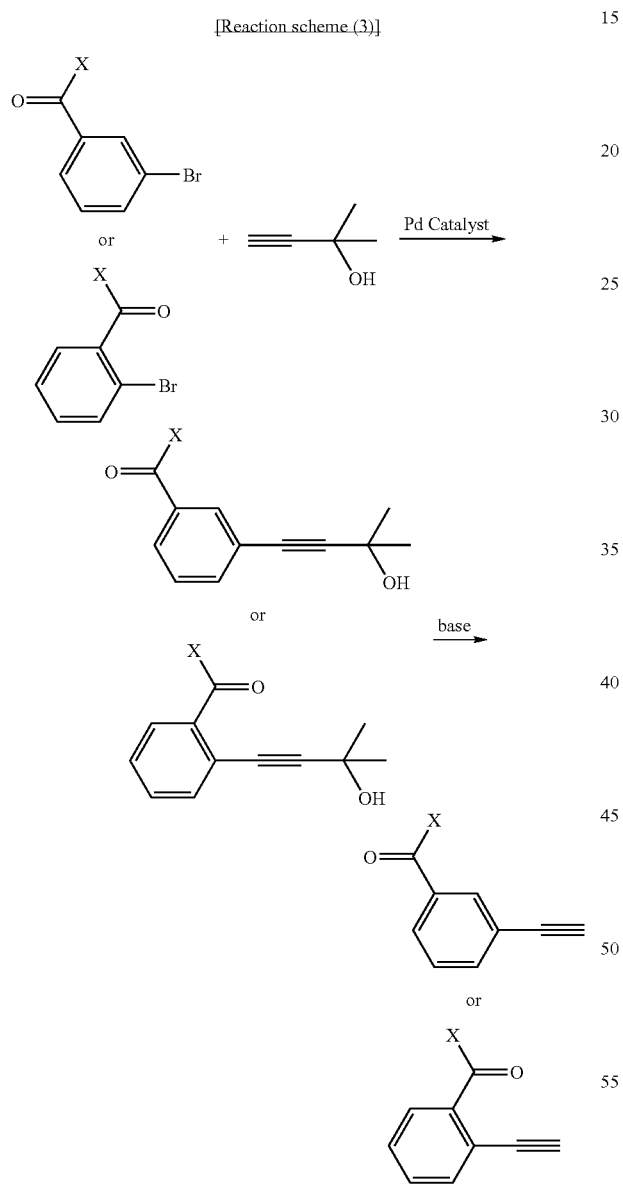

wherein X is as defined above,
by a known method (for example, Journal of Organic Chemistry, 1985, vol. 50, 1763) from the corresponding substituted phenyl bromide.

Alternatively, the substituted phenylethyn compound can be synthesized by deriving an ethynyl substituted aromatic carboxylic acid (JP 3-227954A) and then deriving the carboxyl group into various carboxylic acid derivatives (Lecture on Experimental Chemistry, Fourth edition, published by Maruzen Co., Ltd., vol. 22, Organic Synthesis IV).

In the synthesis of the substituted phenylethynylgold-nitrogen-containing heterocyclic carbene complex of the present invention, the amount of the nitrogen-containing heterocyclic carbene ligand used is preferably 1 to 3 mol, further preferably 1 to 15 mol relative to 1 mol of the substituted phenylethynylgold-phosphine complex.

With respect to the solvent used in the synthesis of the substituted phenylethynylgold-nitrogen-containing heterocyclic carbene complex of the present invention, there is no particular limitation as long as the solvent does not inhibit the reaction and there is used, for example, an ether such as tetrahydrofuran, furan, dioxane, tetrahydropyran, diethyl ether, diisopropyl ether and dibutyl ether, an aliphatic hydrocarbon such as pentane, hexane, heptane and octane; an aromatic hydrocarbon such as benzene, toluene and xylene; a halogenated aliphatic hydrocarbon such as dichloromethane, dichloroethane and dichloropropane; or a halogenated aromatic hydrocarbon such as chlorobenzene. These solvents can be used individually or in combination.

The amount of the solvent used is appropriately selected depending on a degree of uniformity or condition of stirring of the reaction mixture and is preferably 1 to 30 L, further preferably 5 to 20 L relative to 1 mol of the substituted phenylethynylgold-phosphine complex.

The substituted phenylethynylgold-nitrogen-containing heterocyclic carbene complex of the present invention is synthesized by, for example, a method in which a substituted ethynylgold-phosphine complex, a nitrogen-containing heterocyclic carbene ligand (formed by reacting a nitrogen-containing heterocyclic hydrohalide with a base) and a solvent are mixed to effect a reaction while stirring. In this method, the reaction temperature is preferably 0 to 120° C., further preferably 20 to 100° C., and, with respect to the reaction pressure, there is no particular limitation.

After completion of the reaction, the substituted phenylethynylgold-nitrogen-containing heterocyclic carbene complex of the present invention is isolated and purified by a known method such as neutralization, extraction, filtration, concentration, distillation, recrystallization, sublimation or chromatography.

Examples of the substituted phenylethynylgold-nitrogen-containing heterocyclic carbene complexes of the present invention include compounds represented by the following formulae (17) to (26).

(17)

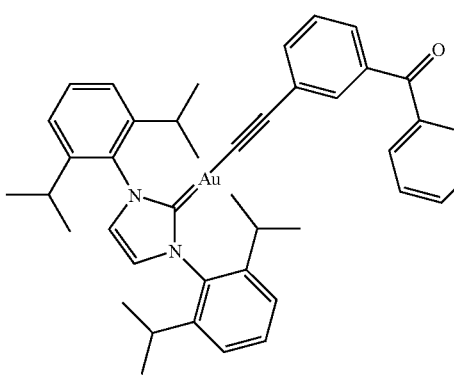

Au(IPr)(3BzPE)

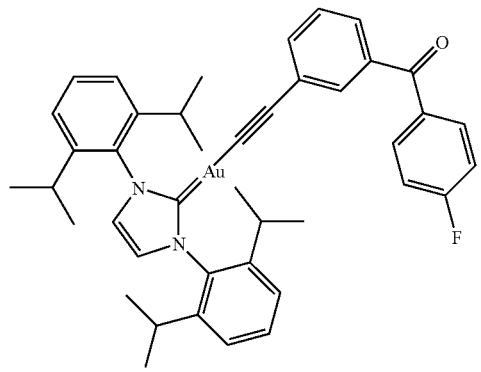
Au(IPr)[3(4'FBz)PE]
(18)
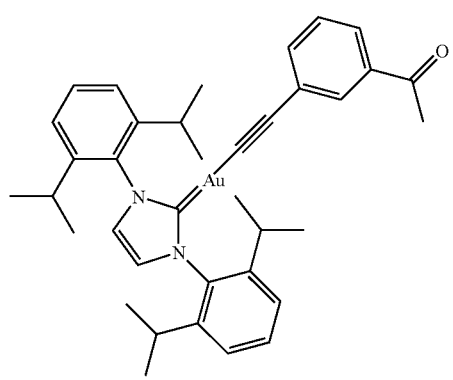
Au(IPr)(3AcPE)
(19)
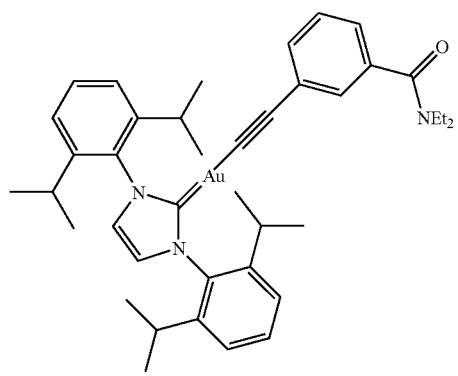
Au(IPr)(3DEACPE)
(20)
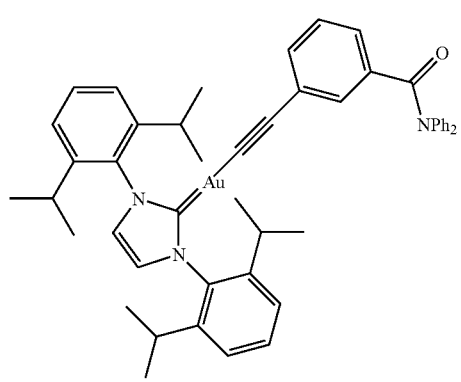
Au(IPr)(3DPACPE)
(21)
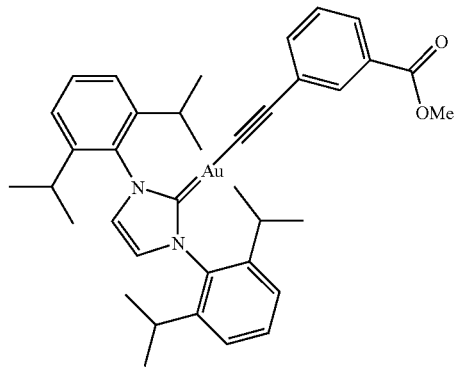
Au(IPr)(3MCPE)
(22)
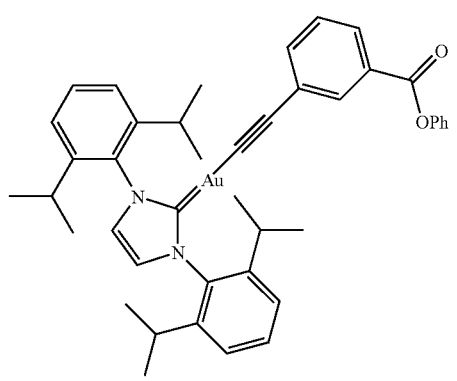
Au(IPr)(3PCPE)
(23)
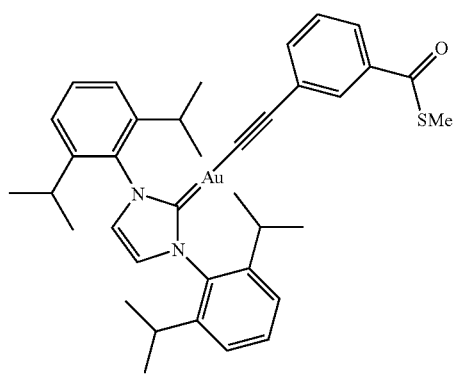
Au(IPr)(3MMCPE)
(24)
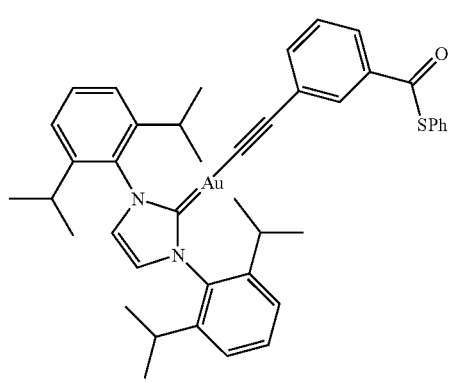
Au(IPr)(3PMCPE)
(25)

-continued (26)

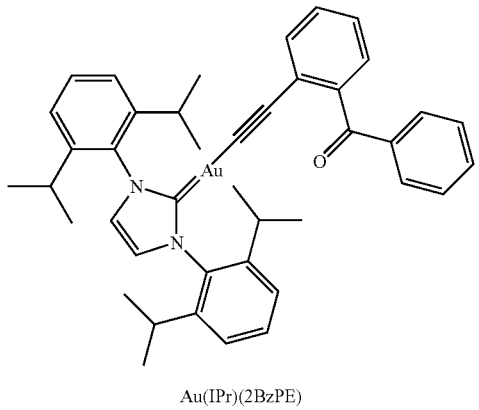

Au(IPr)(2BzPE)

The values for physical properties described in the Examples below suggest that the substituted phenylethynylgold-nitrogen-containing heterocyclic carbene complex of the present invention is advantageously used as an organic electroluminescent device.

EXAMPLES

Hereinbelow, the present invention will be described in more detail with reference to the following Examples, which should not be construed as limiting the scope of the present invention.

Example 1

Synthesis of 3-benzoylphenylethynyl[1,3-bis(2,6-diisopropylphenyl)imidazol-2-ylidene]gold [Au(IPr)(3BzPE)]

In a 20 ml Schlenk tube in an argon atmosphere were charged 1,3-bis(2,6-diisopropylphenyl)imidazolium chloride (IPrH$^+$Cl$^-$; 285 mg, 0.67 mmol), potassium tert-butoxide (85% by mass reagent, 114 mg, 0.86 mmol) and tetrahydrofuran (10 ml) and the mixture was stirred at room temperature for 15 minutes and then tetrahydrofuran was removed by distillation under reduced pressure. To the resultant residue was added toluene (10 ml) and stirred at 70° C. for 5 minutes. Then, the reaction mixture was subjected to filtration and the filtrate was added dropwise to another 30 ml Schlenk tube containing therein 3-benzoylphenylethynyl(triphenylphosphine)gold (340 mg, 0.51 mmol) and 10 ml of toluene. After completion of the dropwise addition, the reaction mixture was heated at 70° C. for 3 hours. The resultant reaction mixture was cooled to room temperature and then toluene was added to the reaction mixture and the mixture was washed with water to make a pH thereof 7. The mixture was dried over sodium sulfate and the solvent was removed by distillation under reduced pressure using an evaporator. The crude reaction product was purified by column chromatography (Hexane/AcOEt=5/1 to 3/1) using silica gel and the resultant solids were washed with hexane and collected by filtration to obtain 0.29 g of a desired product in the form of white solid. (Yield: 72%)
$^1$H-NMR (300 MHz, CDCl$_3$) δ: 7.74-7.12 (m, 17H), 2.64-2.55 (sept, 4H), 1.37 (d, 12H), 1.21 (d, 12H)
EI-MS (M/Z): 790 (M)$^+$
Emission spectral analysis (CHCl$_3$, 77K, Ex 240 nm) λ (nm) 446 (max)

Thermal analysis: Melting point: 224° C.
Elemental Analysis
Measured value C: 63.74, H: 5.58, N: 3.68
Theoretical value C: 63.79, H: 5.74, N: 3.54

Example 2

Synthesis of 3-(4'-fluorobenzoyl)phenylethynyl-[1,3-bis(2,6-diisopropylphenyl)imidazol-2-ylidene]gold [Au(IPr)[3(4 FBz)PE]]

In a 20 ml Schlenk tube in an argon atmosphere were charged 1,3-bis(2,6-diisopropylphenyl)imidazolium chloride (IPrH$^+$Cl$^-$; 259 mg, 0.61 mmol), potassium tert-butoxide (85% by mass reagent, 104 mg, 0.79 mmol) and tetrahydrofuran (10 ml) and the mixture was stirred at room temperature for 15 minutes and then tetrahydrofuran was removed by distillation under reduced pressure. To the resultant residue was added toluene (10 ml) and stirred at 70° C. for 5 minutes. Then, the reaction mixture was subjected to filtration and the filtrate was added dropwise to another 30 ml Schlenk tube containing therein [3-(4'-fluorobenzoyl)phenylethynyl](triphenylphosphine)gold (320 mg, 0.47 mmol) and 10 ml of toluene. After completion of the dropwise addition, the reaction mixture was heated at 70° C. for 3 hours. The resultant reaction mixture was cooled to room temperature and then toluene was added to the reaction mixture and the mixture was washed with water to make a pH thereof 7. The mixture was dried over sodium sulfate and the solvent was removed by distillation under reduced pressure using an evaporator. The crude reaction product was purified by column chromatography (Hexane/AcOEt=5/1) using silica gel and the resultant solids were washed with hexane and collected by filtration to obtain 0.32 g of a desired product in the form of white solid. (Yield: 84%)
$^1$H-NMR (300 MHz, CDCl$_3$) δ: 7.76-7.07 (m, 16H), 2.62-2.56 (sept, 4H), 1.37 (d, 12H), 1.21 (d, 12H)
EI-MS (M/Z); 808 (M)$^+$
Emission spectral analysis (CHCl$_3$, 77K, Ex 240 nm) λ (nm) 442 (max)
Thermal analysis: Melting point: 224° C.
Elemental Analysis
Measured value C: 62.35, H: 5.44, N: 3.44
Theoretical value C: 62.37, H: 5.48, N: 3.46

Example 3

Synthesis of 3-acetylphenylethynyl[1,3-bis(2,6-diisopropylphenyl)imidazol-2-ylidene]gold [Au(IPr)(3AcPE)]

In a 20 ml Schlenk tube in an argon atmosphere were charged 1,3-bis(2,6-diisopropylphenyl)imidazolium chloride (IPrH$^+$Cl$^-$; 272 mg, 0.64 mmol), potassium tert-butoxide (85% by mass reagent, 111 mg, 0.84 mmol) and tetrahydrofuran (10 ml) and the mixture was stirred at room temperature for 15 minutes and then tetrahydrofuran was removed by distillation under reduced pressure. To the resultant residue was added toluene (10 ml) and stirred at 70° C. for 5 minutes. Then, the reaction mixture was subjected to filtration and the filtrate was added dropwise to another 30 ml Schlenk tube containing therein 3-acetylphenylethynyl(triphenylphosphine)gold (298 mg, 0.49 mmol) and 10 ml of toluene. After completion of the dropwise addition, the reaction mixture was heated at 70° C. for 3 hours. The resultant reaction mixture was cooled to room temperature and then toluene was added to the reaction mixture and the mixture was washed with water to make a pH thereof 7. The mixture was dried over sodium sulfate and the solvent was removed by distillation under reduced pressure using an evaporator. The crude reaction product was purified by column chromatography (Hexane/AcOEt=5/1 to 3/1) using silica gel and the resultant solids were washed with hexane and collected by filtration to obtain 0.34 g of a desired product in the form of white solid. (Yield: 95%)

$^1$H-NMR (300 MHz, CDCl$_3$) δ: 7.88-7.13 (m, 12H), 2.65-2.49 (sept, 4H), 2.49 (s, 3H), 1.44 (d, 12H), 1.21 (d, 12H)

EI-MS (M/Z): 728 (M)$^+$

Emission spectral analysis (CHCl$_3$, 77K, Ex 240 nm) λ (nm) 440 (max)

Thermal analysis: Melting point: 224° C.
Elemental Analysis
Measured value C: 60.73, H: 5.95, N: 3.97
Theoretical value C: 60.98, H: 5.95, N: 3.84

Example 4

Synthesis of 3-(diethylaminocarbonyl)phenylethynyl [1,3-bis(2,6-diisopropylphenyl)imidazol-2-ylidene]-gold [Au(IPr)(3DEACPE)]

In a 20 ml Schlenk tube in an argon atmosphere were charged 1,3-bis(2,6-diisopropylphenyl)imidazolium chloride (IPrH$^+$Cl$^-$; 298 mg, 0.70 mmol), potassium tert-butoxide (856 by mass reagent, 120 mg, 0.91 mmol) and tetrahydrofuran (11 ml) and the mixture was stirred at room temperature for 15 minutes and then tetrahydrofuran was removed by distillation under reduced pressure. To the resultant residue was added toluene (11 ml) and stirred at 70° C. for 5 minutes. Then, the reaction mixture was subjected to filtration and the filtrate was added dropwise to another 30 ml Schlenk tube containing therein 3-(diethylaminocarbonyl)phenyl-ethynyl(triphenylphosphine)gold (356 mg, 0.54 mmol) and 11 ml of toluene. After completion of the dropwise addition, the reaction mixture was heated at 70° C. for 3 hours. The resultant reaction mixture was cooled to room temperature and then toluene was added to the reaction mixture and the mixture was washed with water to make a pH thereof 7. The mixture was dried over sodium sulfate and the solvent was removed by distillation under reduced pressure using an evaporator. The crude reaction product was purified by column chromatography (Hexane/AcOEt=5/1 to 1/1) using silica gel and the resultant solids were washed with hexane and collected by filtration to obtain 0.38 g of a desired product in the form of white solid. (Yield: 91%)

$^1$H-NMR (300 MHz, CDCl$_3$) δ: 7.52-7.03 (m, 12H), 3.31 (m, 4H), 2.65-2.54 (sept, 4H), 1.44 (d, 12H), 1.21 (d, 12H), 1.09 (m, 6H)

EI-MS (M/Z): 785 (M)$^+$

Emission spectral analysis (CHCl$_3$, 77K, Ex 240 nm) λ (nm) 421 (max)

Thermal analysis: Melting point: 218° C.
Elemental Analysis
Measured value C: 61.02, H: 6.30, N: 5.32
Theoretical value C: 61.14, H: 6.41, N: 5.35

Example 5

Synthesis of 3-(diphenylaminocarbonyl)phenylethynyl[1,3-bis(2,6-diisopropylphenyl)imidazol-2-ylidene]-gold [Au(IPr)(3DPACPE)]

In a 20 ml Schlenk tube in an argon atmosphere were charged 1,3-bis(2,6-diisopropylphenyl)imidazolium chloride (IPrH$^+$Cl$^-$; 319 mg, 0.75 mmol), potassium tert-butoxide (85% by mass reagent, 129 mg, 0.98 mmol) and tetrahydrofuran (12 ml) and the mixture was stirred at room temperature for 15 minutes and then tetrahydrofuran was removed by distillation under reduced pressure. To the resultant residue was added toluene (12 ml) and stirred at 70° C. for 5 minutes. Then, the reaction mixture was subjected to filtration and the filtrate was added dropwise to another 30 ml Schlenk tube containing therein 3-(diphenylaminocarbonyl)phenyl-ethynyl(triphenylphosphine)gold (356 mg, 0.54 mmol) and 12 ml of toluene. After completion of the dropwise addition, the reaction mixture was heated at 70° C. for 3 hours. The resultant reaction mixture was cooled to room temperature and then toluene was added to the reaction mixture and the mixture was washed with water to make a pH thereof 7. The mixture was dried over sodium sulfate and the solvent was removed by distillation under reduced pressure using an evaporator. The crude reaction product was purified by column chromatography (Hexane/AcOEt=5/1) using silica gel and the resultant solids were washed with hexane and collected by filtration to obtain 0.48 g of a desired product in the form of white solid. (Yield: 95%)

$^1$H-NMR (300 MHz, CDCl$_3$) δ: 7.54-6.83 (m, 22H), 2.62-2.55 (sept, 4H), 1.37 (d, 12H), 1.21 (d, 12H)

EI-MS (M/z): 881 (M)$^+$

Emission spectral analysis (CHCl$_3$, 77K, Ex 240 nm) λ (nm) 427 (max)

Thermal analysis: Melting point: 260° C.
Elemental Analysis
Measured value C: 65.23, H: 5.62, N: 4.87
Theoretical value C: 65.37, H: 5.71, N: 4.76

Example 6

Synthesis of 3-(methoxycarbonyl)phenylethynyl-[1,3-bis(2,6-diisopropylphenyl)imidazol-2-ylidene]gold [Au(IPr)(3MCPE)]

In a 20 ml Schlenk tube in an argon atmosphere were charged 1,3-bis(2,6-diisopropylphenyl)imidazolium chloride (IPrH$^+$Cl$^-$; 282 mg, 0.66 mmol), potassium tert-butoxide (85% by mass reagent, 114 mg, 0.86 mmol) and tetrahydrofuran (10 ml) and the mixture was stirred at room temperature for 15 minutes and then tetrahydrofuran was removed by distillation under reduced pressure. To the resultant residue was added toluene (10 ml) and stirred at 70° C. for 5 minutes. Then, the reaction mixture was subjected to filtration and the filtrate was added dropwise to another 30 ml Schlenk tube containing therein 3-(methoxycarbonyl)phenylethynyl (triphenylphosphine)gold (315 mg, 0.51 mmol) and 10 ml of toluene. After completion of the dropwise addition, the reaction mixture was heated at 70° C. for 3 hours. The resultant reaction mixture was cooled to room temperature and then toluene was added to the reaction mixture and the mixture was washed with water to make a pH thereof 7. The mixture was dried over sodium sulfate and the solvent was removed by distillation under reduced pressure using an evaporator. The crude reaction product was purified by column chromatography (Hexane/AcOEt=5/1) using silica gel and the resultant solids were washed with hexane and collected by filtration to obtain 0.31 g of a desired product in the form of white solid. (Yield: 00W)

$^1$H-NMR (300 MHz, CDCl$_3$) δ: 7.98-7.12 (ml 12H), 3.83 (s, 3H) 2.67-2.54 (sept, 4H), 1.38 (d, 12H), 1.23 (d, 12H)

EI-MS (M/Z): 744 (M)$^+$

Emission spectral analysis (CHCl$_3$, 77K, Ex 240 nm) λ (nm) 426 (max)

Thermal analysis: Melting point: 205° C.
Elemental Analysis
Measured value C: 59.75, H: 5.69, N: 3.77
Theoretical value C: 59.67, H: 5.82, N: 3.76

Example 7

Synthesis of 3-(phenoxycarbonyl)phenylethynyl-[1,
3-bis(2,6-diisopropylphenyl)imidazol-2-ylidene]gold
[Au(IPr)(3PCPE)]

In a 20 ml Schlenk tube in an argon atmosphere were charged 1,3-bis(2,6-diisopropylphenyl)imidazolium chloride (IPrH$^+$Cl$^-$; 212 mg, 0.50 mmol), potassium tert-butoxide (85% by mass reagent, 86 mg, 0.65 mmol) and tetrahydrofuran (8 ml) and the mixture was stirred at room temperature for 15 minutes and then tetrahydrofuran was removed by distillation under reduced pressure. To the resultant residue was added toluene (8 ml) and stirred at 70° C. for 5 minutes. Then, the reaction mixture was subjected to filtration and the filtrate was added dropwise to another 30 ml Schlenk tube containing therein 3-(phenoxycarbonyl)phenylethynyl-(triphenylphosphine)gold (260 mg, 0.38 mmol) and 8 ml of toluene. After completion of the dropwise addition, the reaction mixture was heated at 70° C. for 3 hours. The resultant reaction mixture was cooled to room temperature and then toluene was added to the reaction mixture and the mixture was washed with water to make a pH thereof 7. The mixture was dried over sodium sulfate and the solvent was removed by distillation under reduced pressure using an evaporator. The crude reaction product was purified by column chromatography (Hexane/AcOEt=5/1) using silica gel and the resultant solids were washed with hexane and collected by filtration to obtain 0.22 g of a desired product in the form of white solid. (Yield: 70%)

$^1$H-NMR (300 MHz, CDCl$_3$) δ: 8.16-7.13 (m, 17H), 2.63-2.56 (sept, 4H), 1.38 (d, 12H), 1.22 (d, 12H)
EI-MS (M/Z): 806 (M)$^+$
Emission spectral analysis (CHCl$_3$, 77K, Ex 240 nm) λ (nm) 427 (max)
Thermal analysis: Melting point: 224° C.
Elemental Analysis
Measured value C: 62.17, H, 5.52, N: 3.48
Theoretical value C: 62.53, H: 5.62, N: 3.47

Example 8

Synthesis of 3-(methylmercaptocarbonyl)phenyl-
ethynyl[1,3-bis(2,6-diisopropylphenyl)imidazol-2-
ylidene]-gold [Au(IPr)(3MMCPE)]

In a 20 ml Schlenk tube in an argon atmosphere were charged 1,3-bis(2,6-diisopropylphenyl)imidazolium chloride (IPrH$^+$Cl$^-$; 221 mg, 0.52 mmol), potassium tert-butoxide (85% by mass reagent, 90 mg, 0.68 mmol) and tetrahydrofuran (8 ml) and the mixture was stirred at room temperature for 15 minutes and then tetrahydrofuran was removed by distillation under reduced pressure. To the resultant residue was added toluene (8 ml) and stirred at 70° C. for 5 minutes. Then, the reaction mixture was subjected to filtration and the filtrate was added dropwise to another 30 ml Schlenk tube containing therein 3-(methylmercaptocarbonyl)phenyl-ethynyl(triphenylphosphine)gold (256 mg, 0.4 mmol) and 8 ml of toluene. After completion of the dropwise addition, the reaction mixture was heated at 70° C. for 3 hours. The resultant reaction mixture was cooled to room temperature and then toluene was added to the reaction mixture and the mixture was washed with water to make a pH thereof 7. The mixture was dried over sodium sulfate and the solvent was removed by distillation under reduced pressure using an evaporator. The crude reaction product was purified by column chromatography (Hexane/AcOEt=5/1) using silica gel and the resultant solids were washed with hexane and collected by filtration to obtain 0.22 g of a desired product in the form of white solid. (Yield: 73%)

$^1$H-NMR (300 MHz, CDCl$_3$) δ: 7.91-7.13 (m, 12H), 2.67-2.54 (sept, 4H), 2.40 (s, 3H), 1.38 (d, 12H), 1.22 (d, 12H)
EI-MS (M/Z): 760 (M)$^+$
Emission spectral analysis (CHCl$_3$, 77K, Ex 240 nm) λ (nm): 434 (max)
Thermal analysis: Melting point: 212° C.
Elemental Analysis
Measured value C: 58.15, H: 5.70, N: 3.80
Theoretical value C: 58.41, H: 5.70, N: 3.68

Example 9

Synthesis of 3-(phenylmercaptocarbonyl)phenylethy-
nyl[1,3-bis(2,6-diisopropylphenyl)imidazol-2-
ylidene]-gold [Au(IPr)(3PMCPE)]

In a 20 ml Schlenk tube in an argon atmosphere were charged 1,3-bis(2,6-diisopropylphenyl)imidazolium chloride (IPrH$^+$Cl$^-$; 212 mg, 0.50 mmol), potassium tert-butoxide (85% by mass reagent, 206 mg, 0.49 mmol) and tetrahydrofuran (8 ml) and the mixture was stirred at room temperature for 15 minutes and then tetrahydrofuran was removed by distillation under reduced pressure. To the resultant residue was added toluene (8 ml) and stirred at 70° C. for 5 minutes. Then, the reaction mixture was subjected to filtration and the filtrate was added dropwise to another 30 ml Schlenk tube containing therein 3-(phenylmercaptocarbonyl)phenyl-ethynyl(triphenylphosphine)gold (260 mg, 0.37 mmol) and 8 ml of toluene. After completion of the dropwise addition, the reaction mixture was heated at 70° C. for 3 hours. The resultant reaction mixture was cooled to room temperature and then toluene was added to the reaction mixture and the mixture was washed with water to make a pH thereof 7. The mixture was dried over sodium sulfate and the solvent was removed by distillation under reduced pressure using an evaporator. The crude reaction product was purified by column chromatography (Hexane/AcOEt=5/1) using silica gel and the resultant solids were washed with hexane and collected by filtration to obtain 0.17 g of a desired product in the form of white solid. (Yield: 56%)

$^1$H-NMR (300 MHz, CDCl$_3$) δ: 7.99-7.13 μm, 17H), 2.63-2.56 (sept, 4H), 1.39 (d, 12H), 1.22 (d, 12H)
EI-MS (M/Z): 822 (M)$^+$
Emission spectral analysis (CHCl$_3$, 77K, Ex 240 nm) λ (nm) 435 (max)
Thermal analysis: Melting point: 223° C.
Elemental Analysis
Measured value C: 60.94, H: 5.49, N: 3.50
Theoretical value C: 61.30, H: 5.51, N: 3.40

Example 10

Synthesis of 2-benzoylphenylethynyl[1,3-bis-(2,6-
diisopropylphenyl)imidazol-2-ylidene]gold [Au(IPr)
(2BzPE)]

In a 20 ml Schlenk tube in an argon atmosphere were charged 1,3-bis(2,6-diisopropylphenyl)imidazolium chloride (IPrH$^+$Cl$^-$; 278 mg, 0.66 mmol), potassium tert-butoxide (85% by mass reagent, 112 mg, 0.85 mmol) and tetrahydrofuran (10 ml) and the mixture was stirred at room temperature for 15 minutes and then tetrahydrofuran was removed by distillation under reduced pressure. To the resultant residue was added toluene (10 ml) and stirred at 70° C. for 5 minutes. Then, the reaction mixture was subjected to filtration and the filtrate was added dropwise to another 30 ml Schlenk tube containing therein 2-benzoylphenylethynyl(triphenylphosphine)gold (335 mg, 0.50 mmol) and 10 ml of toluene. After completion of the dropwise addition, the reaction mixture was heated at 70° C. for 3 hours. The resultant reaction mixture was cooled to room temperature and then toluene was added to the reaction mixture and the mixture was washed with water to make a pH thereof 7. The mixture was dried over sodium sulfate and the solvent was removed by distillation under reduced pressure using an evaporator. The crude reaction product was purified by column chromatography (Hexane/AcOEt=5/1) using silica gel and the resultant solids were washed with hexane and collected by filtration to obtain 0.37 g of a desired product in the form of white solid. (Yield: 93%)

$^1$H-NMR (300 MHz, CDCl$_3$) δ: 7.67-7.06 (m, 17H), 2.53-2.44 (sept, 4H), 1.23 (d, 12H), 1.18 (d, 12H)

ET-MS (M/Z): 790 (M)$^+$

Emission spectral analysis (CHCl$_3$, 77K, Ex 240 nm) λ (nm) 457 (max)

Thermal analysis: Melting point: 242° C.

Elemental Analysis

Measured value C: 63.77, H: 5.51, N: 3.54

Theoretical value C: 63.79, H: 5.74, N: 3.54

With respect to each of the substituted phenylethynylgold-nitrogen-containing heterocyclic carbene complexes synthesized in Examples 1 to 10, an emission spectrum was measured by means of a fluorophotometer (in chloroform, at a temperature of 77K (kelvins), under ultraviolet light radiation). Each complex exhibited blue phosphorescence with the emission maximum wavelength of 421 to 457 nm on the CIE chromaticity coordinates (0.149, 0.085) to (0.153, 0.208).

The results of thermal analysis have confirmed that each of the substituted phenylethynylgold-nitrogen-containing heterocyclic carbene complexes of the present invention has a melting point of 200° C. or higher, which suggests that the complex is advantageously used as an organic electroluminescent device.

Reference Example 1

Synthesis of 3-ethynylbenzophenone (First Step)

Air in a 15 ml Schlenk tube was replaced by Ar gas and 1.57 g (6 mmol) of 3-bromobenzophenone, 70 mg (0.06 mmol) of tetrakis(triphenylphosphine)palladium, 6 ml of piperidine and 640 μl (6.6 mmol) of 2-methyl-3-butyn-2-ol were added to the tube and the mixture was stirred at 100° C. for 1.25 hours.

A saturated aqueous ammonium chloride solution was added to the reaction mixture and the mixture was extracted with diethyl ether. The ether layer was dried over magnesium sulfate and the solvent was removed by distillation under reduced pressure using an evaporator. The resultant crude reaction product was purified by column chromatography (Hexane/AcOEt=5/1) using silica gel to obtain 1.46 g of 3-(3-hydroxy-3-methyl-1-butynyl)benzophenone which is a desired product as yellow liquid. (Yield: 92%)

$^1$H-NMR (300 MHz, CDCl$_3$) δ: 7.83-7.40 (m, 9H), 2.09 (s, 1H), 1.61 (s, 6H)

EI-MS (M/Z): 264 (M)$^+$ (Second Step)

In a 100 ml two-necked flask having a reflux condenser were charged 1.45 g (5.5 mmol) of 3-(3-hydroxy-3-methyl-1-butynyl)benzophenone and 230 mg (5.8 mmol) of NaOH (Kishida Chemical Co., Ltd.; 0.7 mm particles, 986) and air in the flask was replaced by Ar gas. 30 ml of toluene was added to the mixture and the mixture was heated at 120° C. under reflux for 0.5 hour. Toluene was added to the reaction mixture and the mixture was washed with a saturated aqueous ammonium chloride solution and dried over magnesium sulfate and the solvent was removed by distillation under reduced pressure using an evaporator. The resultant crude reaction product was purified by column chromatography (Hexane/AcOEt=30/1) using silica gel to obtain 0.9 g of 3-ethynylbenzophenone as orange solid. (Yield: 80%)

$^1$H-NMR (300 MHz, CDCl$_3$) δ: 7.91-7.26 (m, 9H), 3.12 (s, 1H)

ET-MS (M/Z): 206 (M)$^+$

Reference Example 2

Synthesis of 3-ethynyl-4'-fluorobenzophenone (First Step)

Air in a 15 ml Schlenk tube was replaced by Ar gas and 1.4 g (5 mmol) of 3-bromo-4'-fluorobenzophenone, 58 mg (0.05 mmol) of tetrakis(triphenylphosphine)palladium, 5 ml of 1-methylpiperidine and 533 μl (5.5 mmol) of 2-methyl-3-butyn-2-ol were added to the tube and the mixture was stirred at 100° C. for 4.5 hours.

A saturated aqueous ammonium chloride solution was added to the reaction mixture and the mixture was extracted with diethyl ether. The ether layer was dried over magnesium sulfate and the solvent was removed by distillation under reduced pressure using an evaporator. The resultant crude reaction product was purified by column chromatography (Hexane/AcOEt=5/1) using silica gel to obtain 1.11 g of 4-fluoro-3'-(3-hydroxy-3-methyl-1-butynyl)benzophenone which is a desired product as orange crystal. (Yield: 795.)

$^1$H-NMR (300 MHz, CDCl$_3$) δ: 7.83-7.15 (m, R$^H$), 2.15 (s, 1H) 1.62 (s, 6H)

EI-MS (M/Z): 282 (M)$^+$ (Second Step)

In a 100 ml two-necked flask having a reflux condenser were charged 1.11 g (3.9 mmol) of 4-fluoro-3'-(3-hydroxy-3-methyl-1-butynyl)benzophenone and 165 mg (4.1 mmol) of NaOH (Kishida Chemical Co., Ltd.; 0.7 mm particles, 98%) and air in the flask was replaced by Ar gas. 20 ml of toluene was added to the mixture and the mixture was heated at 120° C. under reflux for 0.5 hour. Toluene was added to the reaction mixture and the mixture was washed with a saturated aqueous ammonium chloride solution and dried over magnesium sulfate and the solvent was removed by distillation under reduced pressure using an evaporator. The resultant crude reaction product was purified by column chromatography (hexane/AcOEt=10/1) using silica gel to obtain 0.5 g of 3-ethynyl-4'-fluorobenzophenone as yellow solid. (Yield: 53%)

$^1$H-NMR (300 MHz, CDCl$_3$) δ: 7.87-7.14 (m, 8H), 3.13 (s, 1H)

EI-MS (M/Z): 224 (M)$^+$

Reference Example 3

Synthesis of 3-ethynylacetophenone (First Step)

Air in a 30 ml Schlenk tube was replaced by Ar gas and 1.99 ml (15 mmol) of 3-bromoacetophenone, 173 mg (0.15 mmol) of tetrakis(triphenylphosphine)palladium, 15 ml of piperidine and 1.6 ml (16.5 mmol) of 2-methyl-3-butyn-2-ol were added to the tube and the mixture was stirred at 100° C. for 1.25 hours.

A saturated aqueous ammonium chloride solution was added to the reaction mixture and the mixture was extracted with diethyl ether. The ether layer was dried over magnesium sulfate and the solvent was removed by distillation under reduced pressure using an evaporator. The resultant crude reaction product was purified by column chromatography (Hexane/AcOEt=5/1) using silica gel to obtain 2.98 g of 3-(3-hydroxy-3-methyl-1-butynyl)acetophenone which is a desired product as orange liquid. (Yield: 98%)

$^1$H-NMR (300 MHz, CDCl$_3$) δ: 8.00-7.38 (m, 4H), 2.59 (s, 3H), 2.13 (s, 1H), 1.63 (s, 6H)

EI-MS (M/Z): 202 (M)$^+$ (Second Step)

In a 200 ml two-necked flask having a reflux condenser were charged 2.98 g (14.7 mmol) of 3-(3-hydroxy-3-methyl-1-butynyl)acetophenone and 0.62 g (15.4 mmol) of NaOH (Kishida Chemical Co., Ltd.; 0.7 mm particles, 98%) and air in the flask was replaced by Ar gas. 75 ml of toluene was added to the mixture and the mixture was heated at 120° C. under reflux for 0.5 hour. Toluene was added to the reaction mixture and the mixture was washed with a saturated aqueous ammonium chloride solution and dried over magnesium sulfate and the solvent was removed by distillation under reduced pressure using an evaporator. The resultant crude reaction product was dissolved in 40 ml of hexane at 70° C. and insoluble matter was removed by filtration and then the filtrate was cooled to obtain 3-ethynylacetophenone which is a desired product as white solid. (1.43 g; Yield: 67%)

$^1$H-NMR (300 MHz, CDCl$_3$) δ: 8.07-7.39 (m, 4H), 3.14 (s, 1H) 2.61 (s, 3H)

EI-MS (M/Z).: 144 (M)$^+$

Reference Example 4

Synthesis of 3-ethynyl-N,N-diethylbenzamide

Air in a 20 ml Schlenk tube was replaced by Ar gas and 1.02 g (7 mmol) of m-ethynylbenzoic acid and 5 g (42 mmol) of thionyl chloride were added to the tube and the mixture was stirred at 50° C. for 2 hours and then excess thionyl chloride was removed by distillation under reduced pressure to obtain m-ethynylbenzoyl chloride. To the m-ethynylbenzoyl chloride obtained was added a solution having 1.49 ml (14.4 mmol) of diethylamine dissolved in 7 ml of dichloromethane under ice-cooling and then the resultant mixture was stirred at room temperature for one hour. After completion of the stirring, dichloromethane was removed by distillation under reduced pressure and 35 ml of water was added to the resultant residue. The mixture was extracted with 35 ml of diethyl ether, the ether layer was dried over magnesium sulfate and the solvent was removed by distillation under reduced pressure using an evaporator. The resultant crude reaction product was purified by column chromatography (Hexane/AcOEt=5/1 to 3/1) using silica gel to obtain 1.3 g of 3-ethynyl-N,N-diethylbenzamide which is a desired product as pale yellow liquid. (Yield: 92%)

$^1$H-NMR (300 MHz, CDCl$_3$) δ: 7.76-7.22 μm, 4H), 3.54 (m, 2H), 3.25 (m, 2H), 3.11 (s, 1H), 1.26 (m, 3H) 1.11 (m, 3H)

EI-MS (M/Z): 201 (M)$^+$

Reference Example 5

Synthesis of 3-ethynyl-N,N-diphenylbenzamide

Air in a 20 ml Schlenk tube was replaced by Ar gas and 1.02 g (7 mmol) of m-ethynylbenzoic acid and 5 g (42 mmol) of thionyl chloride were added to the tube and the mixture was stirred at 50° C. for 2 hours and then excess thionyl chloride was removed by distillation under reduced pressure to obtain m-ethynylbenzoyl chloride. To the m-ethynylbenzoyl chloride obtained was added a solution having 2.44 g (14.4 mmol) of diphenylamine dissolved in 7 ml of dichloromethane under ice-cooling and then the resultant mixture was stirred at room temperature for one hour. After completion of the stirring, dichloromethane was removed by distillation under reduced pressure and 35 ml of water was added to the resultant residue. The mixture was extracted with 35 ml of ethyl acetate, the extract was dried over magnesium sulfate and the solvent was removed by distillation under reduced pressure using an evaporator. The resultant crude reaction product was purified by column chromatography (hexane/AcOEt10/1) using silica gel to obtain 0.7 g of 3-ethynyl-N,N-diphenylbenzamide which is a desired product as pale yellow liquid. (Yield: 35%)

$^1$H-NMR (300 MHz, CDCl$_3$) δ: 7.63-6.91 (m, 14H), 3.03 (s, 1H)

EI-MS (M/z): 297 (M)$^+$

Reference Example 6

Synthesis of ethyl 3-ethynylbenzoate

Air in a 20 ml Schlenk tube was replaced by Ar gas and 1.02 g (7 mmol) of m-ethynylbenzoic acid and 5 g (42 mmol) of thionyl chloride were added to the tube and the mixture was stirred at 50° C. for 2 hours and then excess thionyl chloride was removed by distillation under reduced pressure to obtain m-ethynylbenzoyl chloride. To the m-ethynylbenzoyl chloride obtained was added a solution having 298 μl (7.35 mmol) of methanol and 3.4 ml (42 mmol) of pyridine dissolved in 7 ml of dichloromethane under ice-cooling and then the resultant mixture was stirred at room temperature for one hour. After completion of the stirring, dichloromethane was removed by distillation under reduced pressure and 35 ml of water was added to the resultant residue and extracted with 35 ml of diethyl ether. The ether layer was dried over magnesium sulfate and the solvent was removed by distillation under reduced pressure using an evaporator. The resultant crude reaction product was dissolved in 15 ml of hexane at 70° C., insoluble matter was removed by filtration and the filtrate was cooled to obtain 0.74 g of ethyl 3-ethynylbenzoate which is a desired product as yellow solid. (Yield: 66E)

$^1$H-NMR (300 MHz, CDC$_3$) δ: 8.17-7.38 (m, 4H), 3.95 (s, 3H), 3.11 (s, 1H)

EI-MS (M/z): 160 (M)$^+$

Reference Example 7

Synthesis of phenyl 3-ethynylbenzoate

Air in a 20 ml Schlenk tube was replaced by Ar gas and 1.02 g (7 mmol) of m-ethynylbenzoic acid and 5 g (42 mmol) of thionyl chloride were added to the tube and the mixture was stirred at 50° C. for 2 hours and then excess thionyl chloride was removed by distillation under reduced pressure to obtain m-ethynylbenzoyl chloride. To the m-ethynylbenzoyl chloride obtained was added a solution having 692 mg (7.35 mmol) of phenol and 3.4 ml (42 mmol) of pyridine dissolved in 7 ml of dichloromethane under ice-cooling and then the resultant mixture was stirred at room temperature for one hour. After completion of the stirring, dichloromethane was removed by distillation under reduced pressure and 35 ml of water was added to the resultant residue. The mixture was extracted with 35 ml of ethyl acetate, the extract was dried over magnesium sulfate and the solvent was removed by distillation under reduced pressure using an evaporator. The resultant crude reaction product was purified by column chromatography (Hexane/AcOEt=10/1) using silica gel to obtain 0.55 q of phenyl 3-ethynylbenzoate which is a desired product as yellow solid. (Yield: 35%)

$^1$H-NMR (300 MHz, CDCl$_3$) δ: 8.34-6.69 (m, 9H), 3.15 (s, 1H)

EI-MS (M/Z): 222 (M)$^+$

Reference Example 8

Synthesis of S-methyl 3-ethynyl-thiobenzoate

Air in a 20 ml Schlenk tube was replaced by Ar gas and 1.02 g (7 mmol) of m-ethynylbenzoic acid and 5 g (42 mmol) of thionyl chloride were added to the tube and the mixture was stirred at 50° C. for 2 hours and then excess thionyl chloride was removed by distillation under reduced pressure to obtain m-ethynylbenzoyl chloride. To the m-ethynylbenzoyl chloride obtained was added 7 ml of dichloromethane and the resultant mixture was ice-cooled. Then, 515 mg (7.35 mmol) of sodium methanethiolate was added to the mixture and the mixture was stirred at room temperature for 3 hours. After completion of the stirring, dichloromethane was removed by distillation under reduced pressure and 35 ml of water was added to the resultant residue. The mixture was extracted with 35 ml of ethyl acetate and the extract was dried over magnesium sulfate and the solvent was removed by distillation under reduced pressure using an evaporator. The resultant crude reaction product was purified by column chromatography (Hexane/AcOEt=10/1) using silica gel to obtain 0.49 g of S-methyl 3-ethynyl-thiobenzoate which is a desired product as yellow solid. (Yield: 40%)

$^1$H-NMR (300 MHz, CDCl$_3$) δ: 8.09-7.39 (m, 4H), 3.14 (s, 1H), 2.48 (s, 3H)

EI-MS (M/Z): 176 (M)$^+$

Reference Example 9

Synthesis of S-phenyl 3-ethynyl-thiobenzoate

Air in a 20 ml Schlenk tube was replaced by Ar gas and 1.02 g (7 mmol) of m-ethynylbenzoic acid and 5 g (42 mmol) of thionyl chloride were added to the tube and the mixture was stirred at 50° C. for 2 hours and then excess thionyl chloride was removed by distillation under reduced pressure to obtain m-ethynylbenzoyl chloride. To the m-ethynylbenzoyl chloride obtained was added 7 ml of THF and the resultant mixture was ice-cooled. Then, 971 mg (7.35 mmol) of sodium benzenethiol was added to the mixture and the resultant mixture was stirred at room temperature for 2 hours. After completion of the stirring, THF was removed by distillation under reduced pressure and 35 ml of water was added to the resultant residue. The mixture was extracted with 35 ml of ethyl acetate, the extract was dried over magnesium sulfate and the solvent was removed by distillation under reduced pressure using an evaporator. The resultant crude reaction product was purified by column chromatography (Hexane/AcOEt=20/1) using silica gel to obtain 0.51 g of S-phenyl 3-ethynyl-thiobenzoate which is a desired product as yellow solid. (Yield: 31%)

$^1$H-NMR (300 MHz, CDCl$_3$) δ: 8.15-7.39 (m, 9H), 3.16 (s, 1H)

EI-MS (M/Z): 238 (M)$^+$

Reference Example 10

Synthesis of (3-benzoylphenylethynyl)(triphenylphosphine)gold [Au(PPh$_3$)(3BzPE)]

In a 30 ml Schlenk tube in an argon gas atmosphere were charged Au(PPh$_3$)Cl (297 mg, 0.60 mmol), 3-ethynyl-benzophenone (186 mg, 0.9 mmol) and ethanol (12 ml), and then sodium ethoxide (247 μl, 0.63 mmol: ethanol solution having a concentration of 2.55 mol/L (liter)) was added dropwise to the mixture and the mixture was stirred at room temperature for 17 hours. After completion of the reaction, the resultant white precipitate was collected by filtration, washed successively with ethanol (12 ml×3 times), water (12 ml×3 times) and ethanol (6 ml×3 times), and subjected to vacuum drying to obtain 0.38 g of a desired compound as white powder. (Yield: 96%)

$^1$H-NMR (300 MHz, CDCl$_3$) δ: 7.88-7.26 (m, 24H)

FAB-MS (M/Z): 665 (M+H)$^+$

Emission spectral analysis (CHCl$_3$, 77K, Ex 240 nm) λ (nm) 441 (max)

Elemental Analysis
Measured value C: 59.57, H: 3.57
Theoretical value C: 59.65, H: 3.64

Reference Example 11

Synthesis of 3-(4'-fluorobenzoyl)phenylethynyl (triphenylphosphine)gold [Au(PPh$_3$)[3(4'FBz)PE]]

In a 30 ml Schlenk tube in an argon atmosphere were charged Au(PPh$_3$)Cl (297 mg, 0.60 mmol), 3-ethynyl-4'-fluorobenzophenone (202 mg, 0.9 mmol) and ethanol (12 ml), and then sodium ethoxide (247 μl, 0.63 mmol: ethanol solution having a concentration of 2.55 mol/L (liter)) was added dropwise to the mixture and the mixture was stirred at room temperature for 17 hours. After completion of the reaction, the resultant white precipitate was collected by filtration, washed successively with ethanol (12 ml×3 times), water (12 ml×3 times) and ethanol (6 ml×3 times), and subjected to vacuum drying to obtain 0.36 g of a desired compound as white powder. (Yield: 89%)

$^1$H-NMR (300 MHz, CDCl$_3$) δ: 7.86-7.11 (m, 23H)

FAB-MS (M/Z): 683 (M+H)$^+$

Emission spectral analysis (CHCl$_3$, 77K, Ex 240 nm) λ (nm) 424 (max)

Elemental Analysis
Measured value C: 58.26, H: 3.32
Theoretical value C: 58.08, H: 3.40

Reference Example 12

Synthesis of 3-acetylphenylethynyl(triphenylphosphine)gold [Au(PPh$_3$)(3AcPE)]

In a 30 ml Schlenk tube in an argon atmosphere were charged Au(PPh$_3$)Cl (297 mg, 0.60 mmol), 3-ethynylacetophenone (130 mg, 0.9 mmol) and ethanol (12 ml), and then sodium ethoxide (247 μl, 0.63 mmol: ethanol solution having a concentration of 2.55 mol/L (liter)) was added dropwise to the mixture and the mixture was stirred at room temperature for 17 hours. After completion of the reaction, the resultant white precipitate was collected by filtration, washed successively with ethanol (12 ml×3 times), water (12 ml×3 times) and ethanol (6 ml×3 times), and subjected to vacuum drying to obtain 0.34 g of a desired compound as white powder. (Yield: 94%)

$^1$H-NMR (300 MHz, CDCl$_3$) δ: 8.09-7.26 (m, 19H), 2.57 (s, 3H)

FAB-MS (M/Z): 603 (M+H)$^+$

Emission spectral analysis (CHCl$_3$, 77K, Ex 240 nm) λ (nm) 434 (max)

Elemental Analysis

Measured value C: 55.74, H: 3.73

Theoretical value C: 55.83, H: 3.68

Reference Example 13

Synthesis of 3-(diethylamino-carbonyl)phenylethynyl(triphenylphosphine)gold [Au(PPh$_3$)(3DEACPE)]

In a 30 ml Schlenk tube in an argon atmosphere were charged Au(PPh$_3$)Cl (297 mg, 0.60 mmol), 3-ethynyl-N,N-diethylbenzamide (181 mg, 0.9 mmol) and ethanol (12 ml), and then sodium ethoxide (247 µl, 0.63 mmol: ethanol solution having a concentration of 2.55 mol/L (liter)) was added dropwise to the mixture and the mixture was stirred at room temperature for 17 hours. Ethanol was removed by distillation under reduced pressure and dichloromethane was added to the resultant residue. The mixture was washed with water and then dried over sodium sulfate, and the solvent was removed by distillation under reduced pressure using an evaporator to obtain 0.36 g of a desired compound as oil. (Yield: 90%)

$^1$H-NMR (300 MHz, CDCl$_3$) δ: 7.59-7.20 (m, 19H), 3.40 (d, 4H) 1.15 (d, 6H)

FAB-MS (M/Z): 660 (M+H)$^+$

Reference Example 14

Synthesis of 3-(diphenylamino-carbonyl)phenylethynyl(triphenylphosphine)gold [Au(PPh$_3$)(3DPACPE)]

In a 30 ml Schlenk tube in an argon atmosphere were charged Au(PPh$_3$)Cl (297 mg, 0.60 mmol), 3-ethynyl-N,N-diphenylbenzamide (268 mg, 0.9 mmol) and ethanol (12 ml) and then sodium ethoxide (247 µl, 0.63 mmol: ethanol solution having a concentration of 2.55 mol/L (liter)) was added dropwise to the mixture and the mixture was stirred at room temperature for 17 hours. After completion of the reaction, the resultant white precipitate was collected by filtration, washed successively with ethanol (12 ml×3 times), water (12 ml×3 times) and ethanol (6 ml×3 times), and subjected to vacuum drying to obtain 0.41 g of a desired compound as white powder. (Yield: 91%)

$^1$H-NMR (300 MHz, CDCl$_3$) δ: 7.67-7.06 (m, 29H)

FAB-MS (M/Z): 756 (M+H)$^+$

Reference Example 15

Synthesis of 3-methoxycarbonylphenylethynyl(triphenylphosphine)gold [Au(PPh$_3$)(3MCPE)]

In a 30 ml Schlenk tube in an argon atmosphere were charged Au(PPh$_3$)Cl (297 mg, 0.60 mmol), ethyl 3-ethynylbenzoate (181 mg, 0.9 mmol) and ethanol (12 ml) and then sodium methoxide (91 µl, 0.63 mmol: methanol solution having a concentration of 6.95 mol/L (liter)) was added dropwise to the mixture and the mixture was stirred at room temperature for 17 hours. After completion of the reaction, the resultant white precipitate was collected by filtration, washed successively with methanol (12 ml×3 times), water (12 ml×3 times) and methanol (6 ml×3 times), and subjected to vacuum drying to obtain 0.33 g of a desired compound as white powder. (Yield: 88%)

$^1$H-NMR (300 MHz, CDCl$_3$) δ: 8.20-7.26 (m, 19H), 3.89 (s, 3H)

FAB-MS (M/Z): 619 (M+H)$^+$

Reference Example 16

Synthesis of 3-(phenoxycarbonyl)phenylethynyl(triphenylphosphine)gold [Au(PPh$_3$)(3PCPE)]

In a 30 ml Schlenk tube in an argon atmosphere were charged Au(PPh$_3$)Cl (297 mg, 0.60 mmol), phenyl 3-ethynylbenzoate (200 mg, 0.9 mmol) and sodium t-butoxide (61 mg, 0.63 mmol), amyl alcohol (12 ml) was added to the mixture, and the resultant mixture was stirred at room temperature for 17 hours. After completion of the reaction, the resultant white precipitate was collected by filtration and washed successively with t-butanol (12 ml×3 times), warm water (12 ml×3 times) and ethanol (6 ml×3 times) and subjected to vacuum drying to obtain 0.27 g of a desired compound as white powder. (Yield: 67%)

$^1$H-NMR (300 MHz, CDCl$_3$) δ: 8.38-7.19 (m, 24H)

FAB-MS (M/Z): 679 (M+H)$^+$

Reference Example 17

Synthesis of 3-(methylmercaptocarbonyl)phenylethynyl(triphenylphosphine)gold [Au(PPh$_3$)(3MMCPE)]

In a 30 ml Schlenk tube in an argon atmosphere were charged Au(PPh$_3$)Cl (297 mg, 0.60 mmol), S-methyl 3-ethynyl-thiobenzoate (159 mg, 0.9 mmol) and sodium t-butoxide (61 mg, 0.63 mmol), amyl alcohol (12 ml) was added to the mixture, and the resultant mixture was stirred at room temperature for 17 hours. After completion of the reaction, the resultant white precipitate was collected by filtration, washed successively with t-butanol (12 ml×3 times), warm water (12 ml×3 times) and ethanol (6 ml×3 times), and subjected to vacuum drying to obtain 0.27 g of a desired compound as white powder. (Yield: 70%)

$^1$H-NMR (300 MHz, CDCl$_3$) δ: 8.14-7.31 (m, 19H), 2.46 (s, 3H)

FAB-MS (M/Z): 635 (M+H)$^+$

Reference Example 18

Synthesis of 3-(phenylmercaptocarbonyl)phenylethynyl(triphenylphosphine)gold [Au(PPh$_3$)(3PMCPE)]

In a 30 ml Schlenk tube in an argon atmosphere were charged Au(PPh$_3$)Cl (297 mg, 0.60 mmol), S-phenyl 3-ethynylthiobenzoate (215 mg, 0.9 mmol) and sodium t-butoxide (61 mg, 0.63 mmol), amyl alcohol (12 ml) was added to the mixture, and the resultant mixture was stirred at room temperature for 17 hours. After completion of the reaction, the resultant white precipitate was collected by filtration, washed successively with t-butanol (12 ml×3 times), warm water (12 ml×3 times) and ethanol (6 ml×3 times), and subjected to vacuum drying to obtain 0.27 g of a desired compound as white powder. (Yield: 65%)

$^1$H-NMR (300 MHz, CDCl$_3$) δ: 8.21-6.99 (m, 24H)

FAB-MS (M/Z): 697 (M+H)$^+$

Reference Example 19

Synthesis of 2-ethynylbenzophenone (First Step)

Air in a 15 ml Schlenk tube was replaced by Ar gas and 2.61 g (10 mmol) of 2-bromobenzophenone, 231 mg (0.2 mmol) of tetrakis(triphenylphosphine)palladium, 10 ml of piperidine and 1.9 ml (20 mmol) of 2-methyl-3-butyn-2-ol were added to the tube and the mixture was stirred at 100° C. for one hour.

A saturated aqueous ammonium chloride solution was added to the reaction mixture and the mixture was extracted with diethyl ether. The ether layer was dried over magnesium sulfate and the solvent was removed by distillation under reduced pressure using an evaporator. The resultant crude reaction product was purified by column chromatography (Hexane/AcOEt=5/1) using silica gel to obtain 2.6 g of 2-(3-hydroxy-3-methyl-1-butynyl)benzophenone which is a desired product as yellow liquid. (Yield: 99%)

$^1$H-NMR (300 MHz, CDCl$_3$) δ: 7.84-7.40 (m, 9H), 1.67 (s, 1H), 1.21 (s, 6H)

EI-MS (M/Z): 264 (M)$^+$ (Second Step)

In a 100 ml two-necked flask having a reflux condenser were charged 2.6 g (9.9 mmol) of dimethylhydroxymethyl-2-benzoylphenylacetylene and 416 mg (10.4 mmol) of NaOH (Kishida Chemical Co., Ltd.; 0.7 mm particles, 98%) and air in the flask was replaced by Ar gas. 50 ml of toluene was added to the mixture and the mixture was heated at 120° C. under reflux for 0.25 hour. Toluene was added to the reaction mixture, and the mixture was washed with a saturated aqueous ammonium chloride solution and dried over magnesium sulfate. The solvent was removed by distillation under reduced pressure using an evaporator. The resultant crude reaction product was purified by column chromatography (Hexane/AcOEt=20/1) using silica gel to obtain 1.7 g of 2-ethynylbenzophenone as orange solid. (Yield: 82%)

$^1$H-NMR (300 MHz, CDCl$_3$) δ: 7.84-7.42 (m, 9H), 3.04 (s, 1H)

EI-MS (M/Z): 206 (M)$^+$

Reference Example 20

Synthesis of 2-benzoylphenylethynyl(triphenylphosphine)gold [Au(PPh$_3$)(2BzPE)]

In a 30 ml Schlenk tube in an argon atmosphere were charged Au(PPh$_3$)Cl (297 mg, 0.60 mmol), 2-ethynylbenzophenone (186 mg, 0.9 mmol) and ethanol (12 ml), and then sodium ethoxide (247 μl, 0.63 mmol: ethanol solution having a concentration of 2.55 mol/L (liter)) was added dropwise to the mixture and the mixture was stirred at room temperature for 17 hours. After completion of the reaction, the resultant white precipitate was collected by filtration, washed successively with ethanol (12 ml×3 times), water (12 ml×3 times) and ethanol (6 ml×3 times), and subjected to vacuum drying to obtain 0.39 g of a desired compound as white powder. (Yield: 97%)

$^1$H-NMR (300 MHz, CUCl$_3$) δ: 7.88-7.25 (m, 24H)

FAB-MS (M/Z): 665 (M+H)$^+$

Emission spectral analysis (CHCl$_3$, 77K, Ex 240 nm) λ (nm) 459 (max)

Elemental Analysis

Measured value C: 59.24, H: 3.62

Theoretical value C: 59.65, H: 3.64

Industrial Applicability

The substituted phenylethynylgold-nitrogen-containing heterocyclic carbene complex of the present invention is advantageously used as, e.g., a luminescent material for electroluminescent device (organic electroluminescent device). Specifically, the substituted phenylethynylgold-nitrogen-containing heterocyclic carbene complex is advantageously used as, e.g., a luminescent material for organic electroluminescent device, having luminescence in a blue wavelength range of 460 nm or less essential to realize a full-color display and having a high melting point of 200° C. or more such that the material can endure Joulean heat generated in the application of a voltage.

The invention claimed is:

1. A substituted phenylethynylgold-nitrogen-containing heterocyclic carbene complex represented by the following general formula (1) or (2):

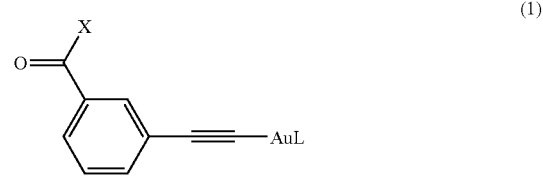

(1)

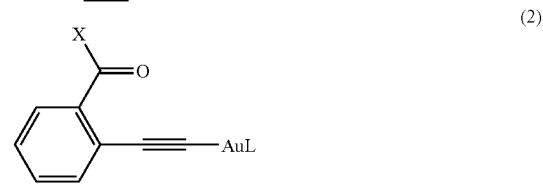

(2)

wherein

L represents a nitrogen-containing heterocyclic carbene ligand represented by the following the general formula (3) or (4):

(3)

(4)

wherein each of R$^1$ and R$^2$ independently represents an alkyl group, a cycloalkyl group, a polycycloalkyl group or an aryl group, and each of R$^3$, R$^4$, R$^5$ and R$^6$ independently represents a hydrogen atom, a halogen atom, an alkyl group, an alkenyl group, an aryl group, an aralkyl group, an alkoxy group, an aryloxy group, a nitro group, a cyano group or a dialkylamino group; the adjacent groups in $R^3$, $R^4$, $R^5$ and $R^6$ are optionally bonded together, so that the adjacent groups and the carbon atom(s) to which the groups are bonded together form a ring; and, when $R^1$ to $R^6$ represent a group containing a carbon atom(s), one hydrogen atom or a plurality of hydrogen atoms on the carbon atom(s) of the group are optionally replaced by a halogen atom, an alkyl group, a cycloalkyl group, an alkenyl group, an aryl group, an aralkyl group, an alkoxy group or an aryloxy group, and X represents an alkyl group, a cycloalkyl group, an aryl group, an aralkyl group, a heterocyclic group, an alkoxy group, an aryloxy group, an alkylmercapto group, an arylmercapto group or a substituted amino group and one hydrogen atom or a plurality of hydrogen atoms on the carbon atom(s) of X are independently optionally replaced by a halogen atom, an alkyl group, a cycloalkyl group, an alkenyl group, an aryl group, an aralkyl group, an alkoxy group, an aryloxy group, an alkylmercapto group, an arylmercapto group or a substituted amino group.

2. The substituted phenylethynylgold-nitrogen-containing heterocyclic carbene complex according to claim 1, wherein each of $R^1$ and $R^2$ represents an alkyl group having 1 to 20 carbon atoms, a cycloalkyl group having 3 to 7 carbon atoms, a polycycloalkyl group having 6 to 10 carbon atoms or an aryl group having 6 to 20 carbon atoms, and each of $R^3$, $R^4$, $R^5$ and $R^6$ represents a hydrogen atom, a halogen atom, an alkyl group having 1 to 20 carbon atoms, an alkenyl group having 2 to 20 carbon atoms, an aryl group having 6 to 20 carbon atoms, an aralkyl group having 7 to 20 carbon atoms, an alkoxy group having 1 to 10 carbon atoms, an aryloxy group having 6 to 14 carbon atoms, a nitro group, a cyano group or a dialkylamino group substituted with the same or different two alkyl groups each having 1 to 6 carbon atoms.

3. The substituted phenylethynylgold-nitrogen-containing heterocyclic carbene complex according to claim 2, wherein the polycycloalkyl group is selected from the group consisting of a bicyclo-[2.1.1]-hexyl group, a bicyclo-[2.2.1]-heptyl group, a bicyclo-[2.2.2]-octyl group, a bicyclo-[3.3.0]-octyl group, a bicyclo-[4.3.0]-nonyl group, a bicyclo-[4.4.0]-decyl group and an adamantyl group.

4. The substituted phenylethynylgold-nitrogen-containing heterocyclic carbene complex according to claim 1, wherein each of $R^1$ and $R^2$ represents a tert-butyl group, a 2,6-diisopropylphenyl group, a 2,4,6-trimethylphenyl group or an adamantyl group, and each of $R^3$, $R^4$, $R^5$ and $R^6$ represents a hydrogen atom or a chlorine atom.

5. The substituted phenylethynylgold-nitrogen-containing heterocyclic carbene complex according to claim 1, wherein each of $R^1$ and $R^2$ represents a tert-butyl group, a 2,6-diisopropylphenyl group, a 2,4,6-trimethylphenyl group or an adamantyl group, and each of $R^3$, $R^4$, $R^5$ and $R^6$ represents a hydrogen atom.

6. The substituted phenylethynylgold-nitrogen-containing heterocyclic carbene complex according claim 1, wherein X is selected from an alkyl group having 1 to 10 carbon atoms; a cycloalkyl group having 3 to 12 carbon atoms; an aryl group having 6 to 18 carbon atoms; an aralkyl group having 7 to 20 carbon atoms; a saturated or unsaturated heterocyclic group containing at least one heteroatom selected from N, O and S and being comprised of a 3- to 10-membered ring; an alkoxy group having 1 to 10 carbon atoms; an aryloxy group having 6 to 14 carbon atoms; an alkylmercapto group having 1 to 6 carbon atoms; an arylmercapto group having 6 to 14 carbon atoms; and an amino group substituted with one group or two groups selected from an alkyl group having 1 to 6 carbon atoms, an aryl group having 6 to 14 carbon atoms and an aralkyl group having 7 to 20 carbon atoms, and one hydrogen atom or a plurality of hydrogen atoms on the carbon atom(s) of X are independently optionally replaced by a fluorine atom, a chlorine atom, a bromine atom, an iodine atom, an alkyl group having 1 to 20 carbon atoms, a cycloalkyl group having 3 to 7 carbon atoms, an alkenyl group having 2 to 20 carbon atoms, an aryl group having 6 to 20 carbon atoms, an aralkyl group having 7 to 20 carbon atoms, an alkoxy group having 1 to 10 carbon atoms, an aryloxy group having 6 to 14 carbon atoms, an alkylmercapto group having 1 to 6 carbon atoms, an arylmercapto group having 6 to 14 carbon atoms or an amino group substituted with one group or two groups selected from an alkyl group having 1 to 6 carbon atoms, an aryl group having 6 to 14 carbon atoms and an aralkyl group having 7 to 20 carbon atoms.

7. The substituted phenylethynylgold-nitrogen-containing heterocyclic carbene complex according to claim 1, wherein X is selected from the group consisting of a phenyl group, a fluorophenyl group, a methyl group, a diethylamino group, a diphenylamino group, a methoxy group, a phenoxy group, a methylmercapto group and a phenylmercapto group.

8. A method for preparing the substituted phenylethynyl-gold-nitrogen-containing heterocyclic carbene complex of claim 1, the method comprising reacting a substituted phenylethynylgold-phosphine complex represented by the following general formula (Ia) or (Ib):

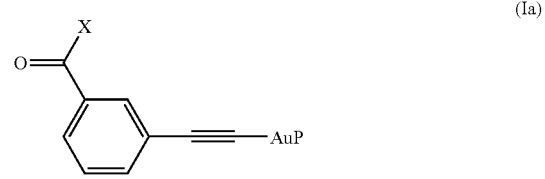

(Ia)

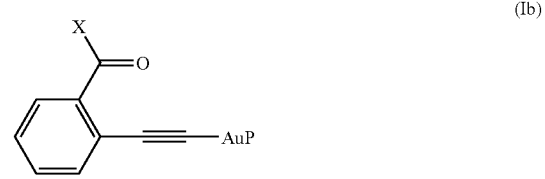

(Ib)

wherein X is the same as defined in claim 1, and P represents a monodentate phosphine ligand, with a nitrogen-containing heterocyclic carbene ligand represented by the following general formula (3) or (4):

(3)

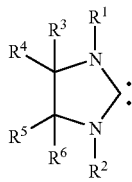 (4)

wherein each of R¹ and R² independently represents an alkyl group, a cycloalkyl group, a polycycloalkyl group or an aryl group, and each of R³, R⁴, R⁵ and R⁶ independently represents a hydrogen atom, a halogen atom, an alkyl group, an alkenyl group, an aryl group, an aralkyl group, an alkoxy group, an aryloxy group, a nitro group, a cyano group or a dialkylamino group; the adjacent groups in R³, R⁴, R⁵ and R⁶ are optionally bonded together, so that the adjacent groups and the carbon atom(s) to which the groups are bonded together form a ring; and, when R¹ to R⁶ represent a group containing a carbon atom(s), one hydrogen atom or a plurality of hydrogen atoms on the carbon atom(s) of the group are optionally replaced by a halogen atom, an alkyl group, a cycloalkyl group, an alkenyl group, an aryl group, an aralkyl group, an alkoxy group or an aryloxy group.

9. The method according to claim 8, wherein the reaction uses 1 to 3 mol of the nitrogen-containing heterocyclic carbene ligand relative to 1 mol of the substituted phenylethynylgold-phosphine complex represented by the general formula (Ia) or (Ib).

10. The method according to claim 8, wherein the reaction is conducted by mixing together the substituted phenylethynylgold-phosphine complex represented by the general formula (Ia) or (Ib) and the nitrogen-containing heterocyclic carbene ligand, and stirring the resultant mixture in the presence of a solvent at a temperature of 0 to 120° C.

* * * * *